US009033953B2

(12) United States Patent
Felber

(10) Patent No.: US 9,033,953 B2
(45) Date of Patent: May 19, 2015

(54) SUCTION PUMP UNIT

(71) Applicant: Medela Holding AG, Baar (CH)

(72) Inventor: Armin Felber, Luzern (CH)

(73) Assignee: Medela Holding AG, Baar (CH)

( * ) Notice: Subject to any disclaimer, the term of this patent is extended or adjusted under 35 U.S.C. 154(b) by 33 days.

(21) Appl. No.: 13/827,069

(22) Filed: Mar. 14, 2013

(65) Prior Publication Data

US 2013/0267933 A1      Oct. 10, 2013

(30) Foreign Application Priority Data

Apr. 4, 2012    (CH) .......................... 474/12

(51) Int. Cl.
| | |
|---|---|
| *A61M 31/00* | (2006.01) |
| *A61M 1/06* | (2006.01) |
| *A61M 1/00* | (2006.01) |
| A61M 39/22 | (2006.01) |

(52) U.S. Cl.
CPC .............. *A61M 1/06* (2013.01); *A61M 1/0037* (2013.01); *A61M 2039/224* (2013.01); *A61M 1/0066* (2013.01)

(58) Field of Classification Search
CPC ... A61M 1/06; A61M 1/0066; A61M 1/0037; A61M 2039/224; A61M 39/22
USPC ..................... 604/28, 30, 33, 74, 249, 514, 35
See application file for complete search history.

(56) References Cited

U.S. PATENT DOCUMENTS

| | | | |
|---|---|---|---|
| 4,070,856 | A | 1/1978 | Litt |
| 4,487,224 | A | 12/1984 | Parker |
| 4,607,596 | A | 8/1986 | Whittlestone et al. |
| 2005/0283112 | A1 | 12/2005 | Britto |
| 2010/0121265 | A1 | 5/2010 | Bryan et al. |
| 2010/0324473 | A1* | 12/2010 | Reznik ............................ 604/28 |

FOREIGN PATENT DOCUMENTS

| | | |
|---|---|---|
| DE | 2347034 | 4/1975 |
| DE | 10228455 | 2/2004 |
| WO | 2011035447 | 3/2011 |

OTHER PUBLICATIONS

International Search Report, PCT/CH2013/000040, mailed May 31, 2013.

* cited by examiner

*Primary Examiner* — Theodore Stigell
(74) *Attorney, Agent, or Firm* — McDonnell Boehnen Hulbert & Berghoff LLP

(57) ABSTRACT

A suction pump unit comprises a vacuum port, an excess pressure port and a switching valve. The switching valve comprises a valve body with two inputs, wherein a first of the inputs is connected with the vacuum port, and a second of the inputs is connected with the excess pressure port. The switching valve further comprises an output with a through hole, wherein the output can be moved relative to the inputs from the first input to the second input and back, as a result of which the through hole alternately establishes a fluid-communicating connection with one of the inputs. The through hole of the output is released and ventilated during at least part of the movement between the two inputs. This suction pump unit permits passive and active ventilation of an output line connected with the output.

22 Claims, 5 Drawing Sheets

SUCTION PUMP UNIT

CROSS-REFERENCE TO RELATED APPLICATIONS

This application claims the benefit of Swiss Patent Application Serial No. 0474/12 filed Apr. 4, 2012, the contents of which are fully incorporated herein by reference.

TECHNICAL AREA

The present invention relates to a suction pump unit as well as to a method for operating a suction pump unit. The suction pump serves in particular for use as a breast pump for extracting human breast milk.

BACKGROUND

Suction pump units are sufficiently known in prior art. They are used for extracting breast milk, but also in the medical field for extracting body liquids or fluids. Examples for the latter include extraction processes during and after surgical procedures, wound drainage, thorax drainage, and the suctioning of body fat.

While pumping breast milk, a vacuum pump is used to create a vacuum in a breast shield applied to the mother's breast, which causes the breast milk to be extracted from the breast. In order to enable as painless a suction as possible that corresponds to the sucking rhythm of the infant, a chronologically changing vacuum is applied to the breast shield. Suction curves that comprise a rapid rise in the vacuum to atmospheric pressure or to some other base value have proven especially effective in practice. FIG. 12 shows a corresponding pressure progression.

It was shown that a rise in pressure in an excess pressure range can be advantageous, as may be gleaned from FIG. 13. For example, one advantage is that any milk that gets into the vacuum tube between the breast shield and the breast pump can be purged. Another advantage is that a relatively thin vacuum tube can be used between the breast shield and the pump aggregate given active ventilation owing to an excess pressure source. Without active ventilation, the flow resistance in the thin tube would be too big, so that it would be impossible to dissipate the vacuum fast enough. Thin tubes yield a small dead volume. This in turn makes it possible to use smaller pump aggregates, i.e., vacuum pumps with a lower suction power.

A pressure progression with a positive ratio can be achieved by using the exhaust of the vacuum pump as a pressure source. However, in order to ensure the functionality of the vacuum pump, one of the pump connections, i.e., the vacuum port or the exhaust, must always be open. This can be accomplished with a 5/2 way valve. But the disadvantage to these valves is that they are relatively large, heavy and expensive. In addition, a steep flank is also preferred for this pressure progression during the rise in pressure. However, such a steep flank is virtually impossible to achieve with 5/2 way valves.

DE 102 28 455 discloses a milk extraction device with a vacuum pump, whose vacuum port and exhaust are connected with a switching valve. A suction line runs from the switching valve to a breast shield. Because the switching valve is connected with the exhaust acting as the excess pressure source, the vacuum in the breast shield can be changed relatively quickly. In this case, the switching valve comprises a rotating disk, which alternately releases a vacuum opening or an excess pressure opening.

US 2010/0121265 describes a breast pump for extracting breast milk with solenoid valves.

The pressure changes achievable by means of known suction pump units with the assistance of an excess pressure source take place relatively slowly. However, rapid changes in pressure are required to enable as natural an extraction as possible. A demand for suction curves with rapidly changing pressure ratios also exists in the other areas of application mentioned above for medical suction pump units.

SUMMARY OF THE INVENTION

Therefore, an object of the invention is to provide a suction pump unit and a method for operating such a suction pump unit that enables a rapid and reliable reduction in the applied vacuum, even when using an excess pressure source.

The suction pump unit according to the invention comprises a vacuum port, an excess pressure port and a switching valve. The switching valve comprises a valve body with two inputs, wherein a first of the inputs is connected with the vacuum port, and a second of the inputs is connected with the excess pressure port. The switching valve further comprises an output with a through hole, wherein the output can be moved relative to the inputs from the first input to the second input and back. Therefore, it can be switched back and forth between these two inputs. As a result, the through hole alternately establishes a fluid-communicating connection with one of the inputs. According to the invention, the through hole of the output is released and ventilated during at least part of the movement between the two inputs.

In one aspect, the output can be lifted relative to the two inputs while moving between the two inputs, wherein the through hole of the output is released and ventilated in the lifted state.

In the method according to the invention for operating a suction pump unit mentioned above, the output is moved back and forth between the two inputs relative to the two inputs. While the output moves, the through hole alternately establishes a fluid-communicating connection with one of the inputs. According to the invention, the through hole of the output is released and ventilated while moving between the two inputs.

According to the invention, the output and an output line connected with this output are already ventilated as soon as the output is removed from the vacuum port and before it is connected with the excess pressure port. As a result, ventilation takes place faster than in conventional 5/2 way valves. FIG. 14 presents a corresponding pressure progression. For example, it is possible to achieve ventilation times, and hence pressure rises in the atmospheric range, which correspond to the classic suction pump units without excess pressure sources. In addition, however, a pressure rise in the positive value range can be obtained.

The steep pressure rise or the ventilation curve makes it possible to achieve shorter cycle times, and hence higher cycle numbers, than in known suction pump units with a positive pressure progression. As a consequence, the pumping frequency can be increased.

This switching valve according to the invention massively expands the range of available suction curves both with respect to possible pumping frequencies and pump delivery rate changes, and with respect to the shape of the curve.

If a membrane is used to separate media, for example as described in WO 2011/035447, the rapid pressure change results in a quick and reliable reset of this membrane. This also makes it possible to use a higher cycle number for the suction curve by comparison to known suction pumps.

It is further advantageous that the switching valve, also referred to as actuator, is relatively small and simple in design. It is correspondingly cost effective. It is further advantageous that it is only a three-way valve.

The output is moved relative to the inputs, meaning that either the output and/or the inputs can be moved. In a preferred embodiment, the valve body is fixed in place with the inputs and situated in the suction pump unit, and the output is moved.

The movement of the output relative to the two inputs in one example embodiment involves a combination of being shifted along a straight line in a first direction and lifted in a second direction perpendicular to the first direction. This movement makes it possible to release the through hole of the output early, wherein already a minimal force is sufficient to detach the output from the corresponding input.

Preferably secured to the output is an output line of the suction pump unit, which can be moved together with the output. This output line leads to the user. In the case of a breast pump unit, it leads to the breast shield. In the case of a drainage pump, it leads to a cavity of the patient to be extracted.

The suction pump unit can comprise a vacuum source and an excess pressure source separated and independent from it. However, in one example embodiment, an exhaust of a vacuum pump is used as the excess pressure source. Therefore, the suction pump unit in a preferred embodiment comprises a single vacuum pump, wherein the vacuum pump comprises the vacuum port, and wherein it further comprises an exhaust that forms the excess pressure port.

In order to keep the relative shifting path of the output as small as possible, the two inputs are arranged next to each other in a plane in one example embodiment.

In one aspect, the two inputs are arranged in a sliding plate with a planar surface, and the output rests upon this sliding plate once the fluid-communicating connection with the inputs has been established. This sliding plate enables a tight connection between the input and the output. If the sliding plate comprises a low static friction coefficient and a low kinetic friction coefficient, the output can be moved relative to the inputs with little exertion of force.

The relative movement of the output in relation to the two inputs can be achieved in different ways. In a preferred embodiment, the switching valve according to the invention is a solenoid valve.

In another aspect, it comprises two electromagnets with one coil each, wherein each coil is interspersed by a ferromagnetic, hollow core. The two hollow cores form the two inputs. The output comprises a permanent magnet. The permanent magnet is preferably a ring that forms the through hole. In preferred exemplary embodiment, the output is formed by a permanent magnet, in particular by the annular embodiment.

In one example embodiment, the coils are arranged so as to run parallel to each other. However, they can also be situated at an angle relative to each other, wherein they approach each other toward the output. This shortens the path over which the output moves back and forth between the two inputs by comparison to the parallel configuration. The switching time is minimized as a result.

The use of electromagnetic coils, in particular cylindrical coils, in the switching valve enables a very rapid switching of the valve. The two coils are exposed to an opposing current. The valve switches over given a change in the two currents. The additional advantage to this embodiment is that it is subject to virtually no material fatigue, and ensures a reliable switching of the valve.

If a permanent magnet is used in the output, the output is attracted by one of the cores with the coils in the currentless state, and closes the valve in this position. The pneumatic tightness is also ensured in this state. The switching valve comprises a low current consumption, since the coils only require current when being changed from a vacuum to a positive pressure and vice versa.

In order to sufficiently guide the output in terms of its relative movement in relation to the two inputs, the two inputs of the valve body are covered by a lid in a preferred embodiment. The lid opens up a hollow space over the inputs. The output is movably held in this hollow space. Air is present in the hollow space for ventilating the output as it moves back and forth. For this purpose, the hollow space is preferably exposed to ambient air, i.e., the valve housing is not tight relative to the environment, or it comprises an air supply opening. Environment is here understood as either the interior of the suction pump unit or the outer environment of the suction pump unit.

So as to be able to lift the connection as it moves back and forth relative to the inputs, the hollow space, in one example embodiment, comprises a height that exceeds a thickness of the connection. Other solutions are also possible, for example a lowering motion of the inputs.

In one example embodiment, the two coils are held in a shared yoke to ensure the stability of the valve, wherein the yoke is arranged at an end of the valve body lying opposite the output.

Instead of being designed as electromagnetic coils, the switching valve can also be configured as a parallelogram. In a preferred embodiment, the switching valve comprises two plates that are arranged parallel to each other and can be shifted parallel to each other, wherein the output is held in a first of these plates, and the two inputs are situated in a second of these plates. The two plates are connected with each other to form a parallelogram, in one example embodiment, by means of flexural elements, in particular leaf springs or surface elements with integral hinges.

In another aspect, the relative movement between the output and the inputs takes place by exerting force on at least one of these two plates to move them in the direction of their plate plane. Preferably, the inputs are held fixedly in place, and the output is moved.

The advantage to the embodiments with the parallelogram is that they are lighter and more cost-effective than the variants with the electromagnetic coils.

Other embodiments are indicated in the dependent claims.

BRIEF DESCRIPTION OF THE DRAWINGS

Preferred embodiments of the invention will be described below based on the drawings, which are only for explanatory purposes, and must not be construed as limiting. The drawings show.

DETAILED DESCRIPTION

Figure 1:
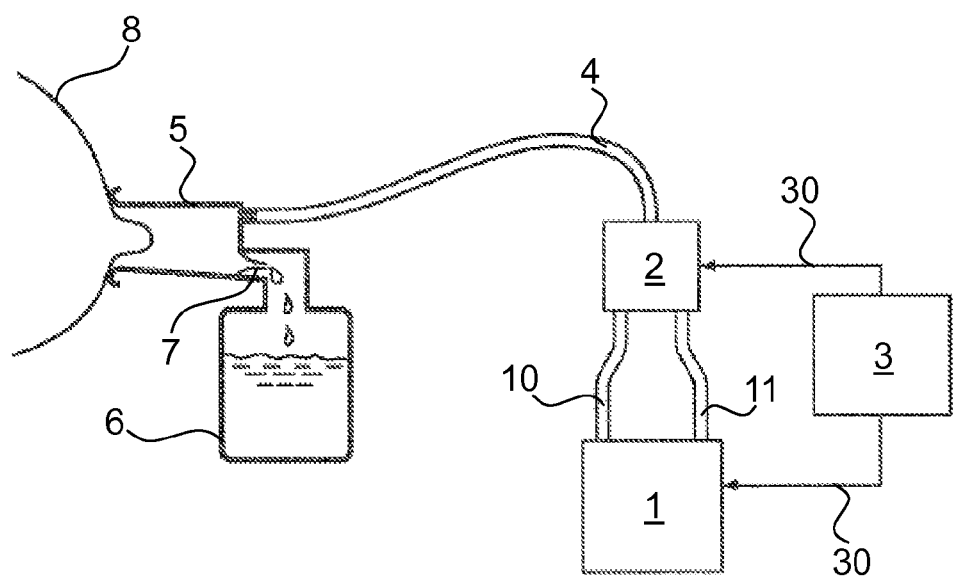
FIG. 1 shows a schematic view of a breast pump unit according to the invention during the extraction of breast milk.
Figure 2:
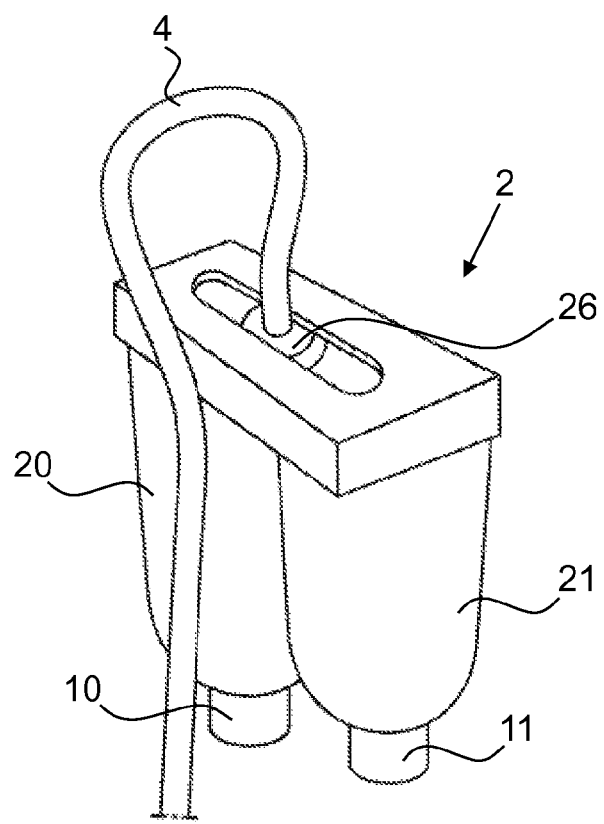
FIG. 2 shows a perspective view of a switching valve according to the invention in a first embodiment.
Figure 3:
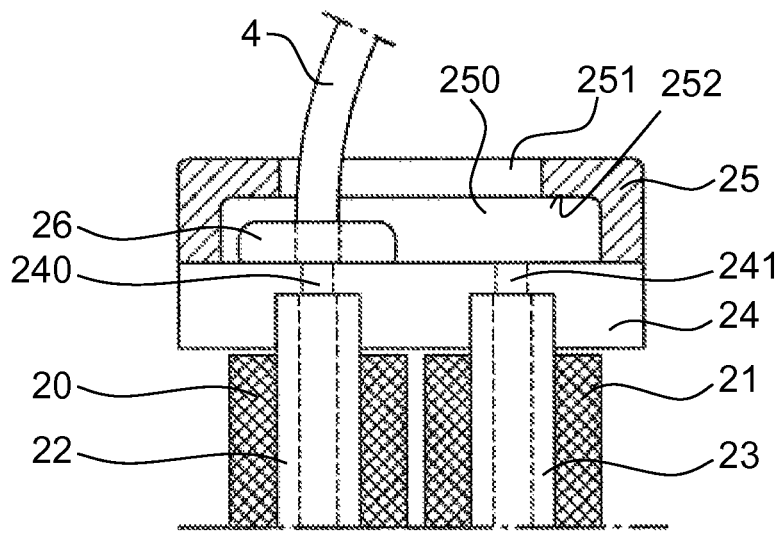
FIG. 3 shows a longitudinal section through the switching valve according to FIG. 2.
Figure 4:
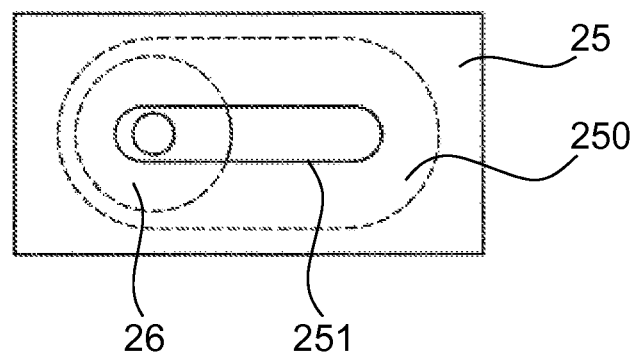
FIG. 4 shows a view from above of the switching valve according to FIG. 2.

FIG. 1 shows a schematic breast pump unit. However, the instruction according to the invention can also be applied to other suction pumps, in particular to drainage pumps. The suction pump unit comprises a suction pump 1, also referred to as vacuum aggregate. The suction pump 1 comprises a suction or a vacuum port and an exhaust for ventilating the suction pump 1. A suction line 10 is hooked up to the suction connection, while a pressure line 11 is hooked up to the exhaust. These two lines 10, 11 lead to a switching valve 2, also referred to as actuator. The suction pump 1 and the switching valve 2 are connected to each other by an electronic controller 3. The connecting lines are depicted schematically, and marked with reference number 30.

An output line 4 leads from the switching valve 2 to a breast shield 5, which is connected with a milk collection container 6. Usually situated between the milk collection container 6 and breast shield 5 is a check valve 7, which limits the dead volume. The human mother's breast upon which the breast shield 5 is placed is here marked with reference number 8. The breast shield 5 can also comprise another shape. Examples of the latter are sufficiently known from prior art. The output line 4 is usually a flexible hose, in particular made out of silicone. However, the suction pump 1 with the switching valve 2 can also be directly secured to the breast shield 5, so that the output line 4 can be omitted or runs inside a housing of a breast shield/suction pump combination.

FIGS. 2 to 7 show a first exemplary embodiment of a switching valve 2 according to the invention. it comprises two electromagnets, i.e., cylindrical coils 20, 21. Ferromagnetic cores 22, 23 run in these coils 20, 21, and are also preferably designed as a hollow cylinder. In particular steel or iron cores are suitable as the cores 22, 23. Therefore, reference is made below to iron cores, wherein the cores can also consist of other suitable materials. These cores 22, 23 form two inputs of the switching valve 2. A first core 22 of the first coil 20 is connected with the suction line 10, while a second core 23 of the second coil 21 is connected with the pressure line 11 of the suction pump 1.

The two coils 20, 21 are held in a yoke 27. The yoke 27 preferably also consists of a ferromagnetic material. The two cores 22, 23 preferably touch or intersperse the yoke 27.

At the opposing end, the two coils 20, 21 are covered by a sliding plate 24. The two cores 22, 23 preferably project into this plate 24. The sliding plate 24, coils 20, 21 and cores 22, 23 comprise a valve body.

The plate 24 comprises through holes 240, 241, wherein a first of these through holes 240 is connected with the first input formed by the first core 22. A second of the through holes 241 is connected with the second input formed by the second core 23. This creates a first fluid-permeable line from the suction connection via the suction line 10 to the first input 22 and to the first through hole 240. A second fluid-permeable line is created from the exhaust via the pressure line 11 to the second input 23 and to the second through hole 241. Both through holes 240, 241 preferably comprise the same diameter. The two inputs 22, 23 also preferably comprise the same diameter. The diameters of the through holes 240, 241 are identical in size to the diameters of the inputs 22, 23, or preferably smaller. However, they are preferably centrally situated on the inputs 22, 23.

The sliding plate 24 preferably consists of plastic, in particular polyamide. It preferably comprises an outwardly directed planar surface. The latter can comprise a low static friction coefficient and a low kinetic friction coefficient at least in the region of the cores 22, 23.

This sliding plate 24 is covered by a lid 25. The lid is preferably made out of plastic, in particular polyamide. It forms a hollow space 250 over the sliding plate 24, which comprises a window, here a slit 251. The window 251 extends at least from the first through hole 240 to the second through hole 241. The window is enveloped by an inwardly directed surface 252 of the lid 25. This surface 252 preferably comprises a low static friction coefficient and a low kinetic friction coefficient.

Situated in the hollow space 250 is a permanent magnet ring 26. It comprises a through hole that approximately corresponds to the through holes 240, 241 of the sliding plate 24. The permanent magnet ring 26 is slidably held in the hollow space 250, wherein the hollow space 250 is dimensioned in such a way that the ring 26 can be moved from the first through hole 240, and hence from the first input 22, to the second through hole 241, and hence to the second input 23, and back again. The magnet ring 26 here covers the respective through hole 240, 241 completely, and forms a fluid-tight connection with the respective input 22, 23.

The magnet ring 26 forms the output of the switching valve 2. The output line 4 is hooked up to the magnet ring. The slit 251 is large enough to allow the output line 4 to move unimpeded when the magnet ring 26 moves. This is readily visible in FIGS. 3 and 4. The output line 4 is preferably led away from the lid 25 in a U-shape, as may be discerned in FIG. 2.

Figure 5:
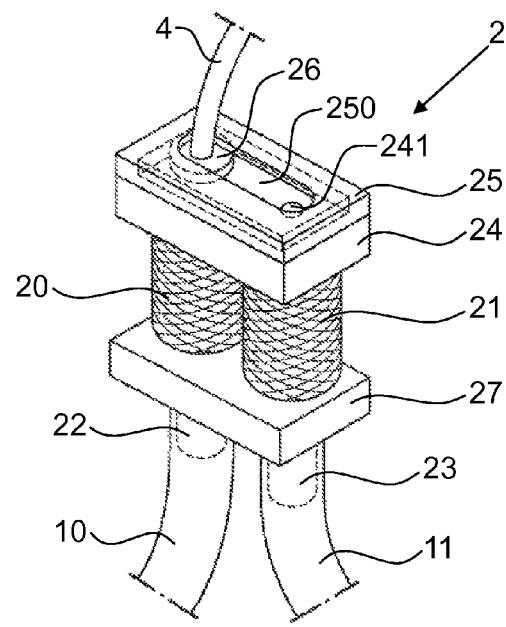
FIG. 5 shows another perspective view of the switching valve according to FIG. 2.
Figures 6, 7:
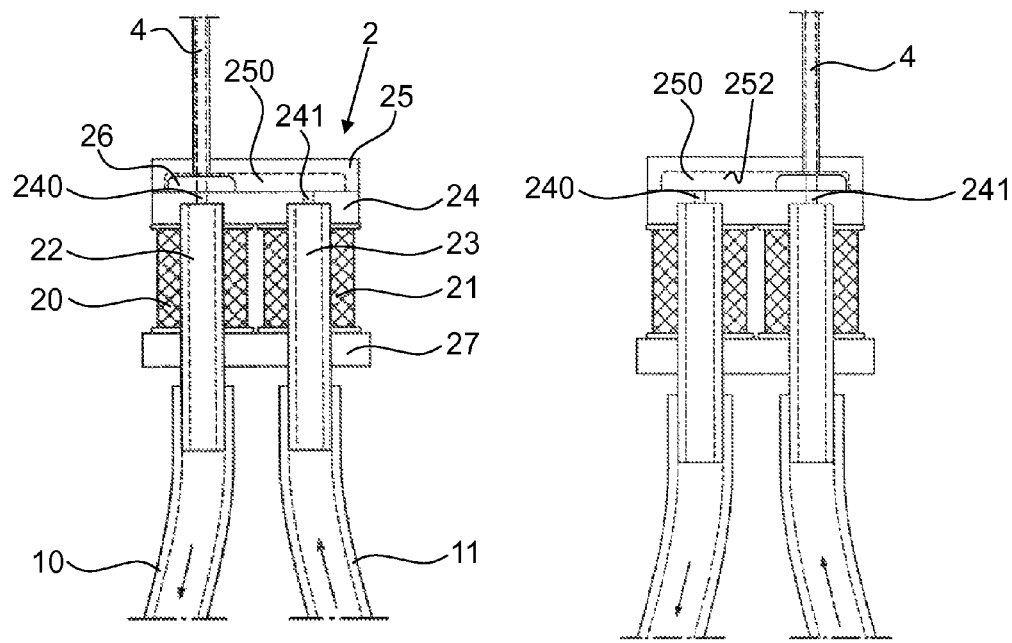
FIG. 6 shows a longitudinal section through the switching valve according to FIG. 2 in a first position of the output.
FIG. 7 shows a longitudinal section through the switching valve according to the invention in a second position of the output.

The described arrangement provides the option of creating a tight line between the suction connection of the vacuum pump 1 and the breast shield 5, and a tight line between the exhaust of the vacuum pump 1 and the breast shield 5. To this end, the coils 20, 21 are briefly exposed to opposing current. The resulting magnetic field generated in the core 22 is polarized opposite to the magnetic field in the second core 23. The magnet ring 26 is attracted by a core 22, and repelled by the other core 23. This situation is illustrated in FIGS. 5 and 6. The suction line 10 is now connected with the breast shield 5.

If the direction of current is switched, i.e., if the polarity of the coils is reversed, the polarity of the magnetic fields is also reversed. The magnet ring 26 is now repelled by the first input 22 and attracted by the second input 23. It moves toward the second input 23, during which it is lifted toward the lid 25, thereby releasing its through hole. The lifting of the magnet ring 26 is limited by the lid 25. This is readily discernible in FIG. 3. The magnet ring 26 here preferably slides along the inwardly directed surface 252 of the lid 25 toward the second input 23, and lowers itself onto this second input 23.

Lifting the output 26 ventilates the magnet ring, i.e., the output 26, and hence the output line 4. At the conclusion of its movement, the magnet ring 26 lies on the second input 23, and forms a fluid-tight line with the latter. The exhaust and the pressure line 11 are now connected with the breast shield 5. The output line 4 and breast shield 5 can be actively ventilated, and even an excess pressure can be generated. Again switching the current in turn moves the magnet ring 26 back to the first input 22. The movement of the magnet ring 26 is here the same as described above, but in the opposite direction.

If no current is flowing, the magnet ring 26 remains in its last position, and continues to form a tight line.

The current is switched, and hence the polarity of the magnetic fields is reversed, based on the controller 3. The most varied of activation patterns are here possible, and can be cyclic, erratic or follow other parameters.

Figure 8:
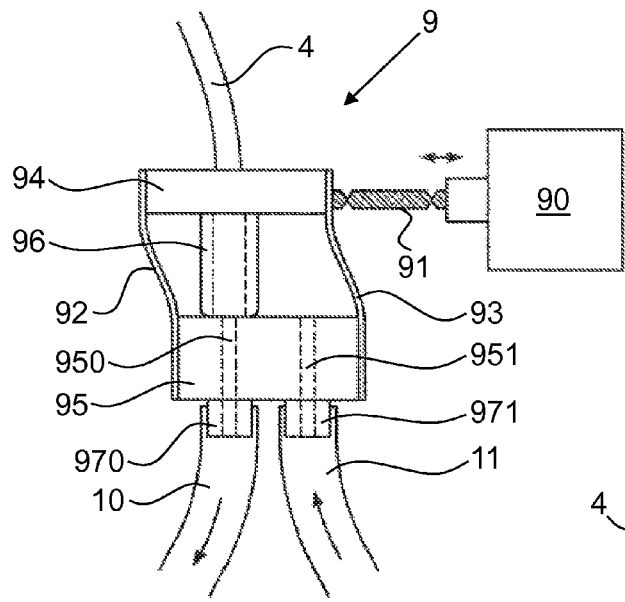
FIG. 8 shows a longitudinal section through the switching valve according to the invention in a second embodiment and in a first position.
Figure 9:
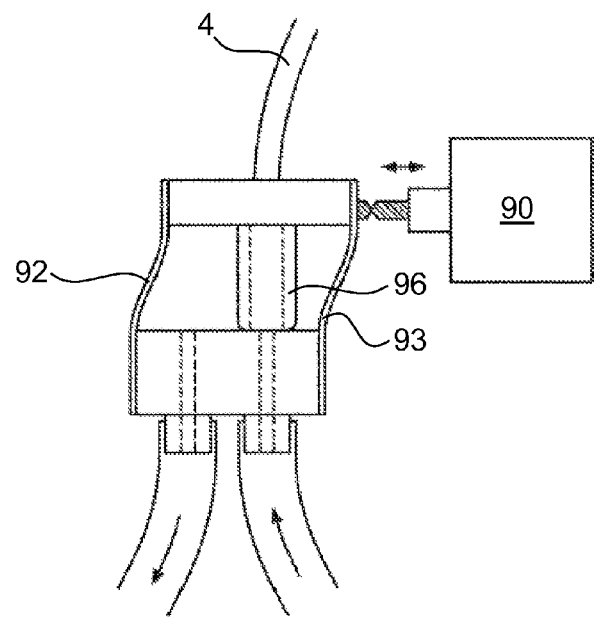
FIG. 9 shows a longitudinal section through the switching valve according to FIG. 8 in a second position.
Figure 10:
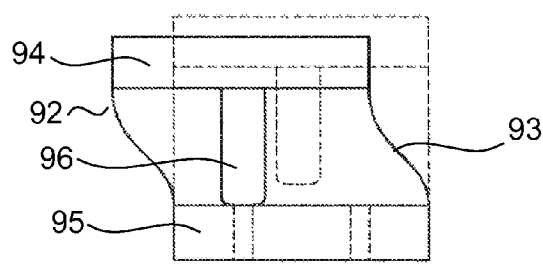
FIG. 10 shows a schematic view of the back and forth movement of the output of the switching valve according to FIG. 8.

FIGS. 8 to 10 describe a second exemplary embodiment of the switching valve according to the invention. Identical parts are marked with the same reference numbers as in the first example.

Present here instead of permanent magnets is a parallelogram 9, which is formed by two plates 94, 95 and two flexible parts 92, 93. The two plates are preferably made out of metal or plastic. The output 96 of the switching valve is arranged on the first plate 94. It is here fixedly secured to the first plate 94. The output 96 is also connected with the output line 4. For example, either the output line 4 and/or the output 96 intersperses the first plate 94. Two inputs in the form of through holes 950, 951 are present in the second plate 95, which forms a valve body.

They are preferably situated next to each other. Connection nozzles 970, 971 are present on the second plate 95, so as to hook up the suction line 10 and the pressure line 11.

The output 96 can again be moved relative to the inputs. A drive 90 is present for this purpose. For example, this drive can be an electric motor. The drive 90 is connected with a driving rod 91, which is fixedly connected with a lateral face of the first plate 94, or abuts the latter. As a consequence, the first plate 94 can be shifted along its plate plane. This causes the output 96 to also shift from the first input 950 according to FIG. 8 to the second input 951 according to FIG. 9.

As in the first exemplary embodiment, the movement involves a combination of a straight shifting in a first direction and a lifting in a second direction perpendicular to the first direction. This is readily visible in FIG. 10.

Even more support is given to the movement if the flexible parts are leaf springs 92, 93 as in this example. It is also possible to use the driving rods 91 only for movement in one direction, and to have the reset take place via the leaf springs. In addition, several driving rods can be used at different force application points of the parallelogram. As an alternative, the second plate 95 can be moved instead of the first plate 94, or in addition to the first plate 94.

Figure 11:
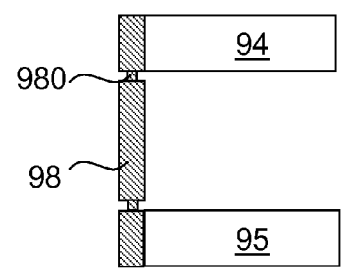
FIG. 11 shows a magnified section of a switching valve according to the invention in a third embodiment.
Figure 12:
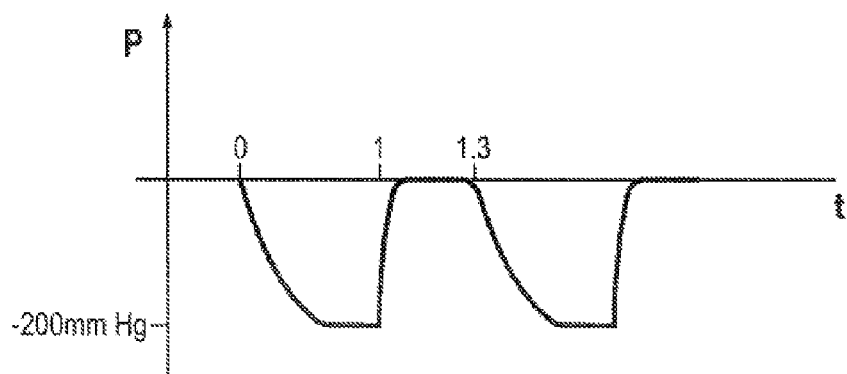
FIG. 12 shows a graphic view of the pressure as a function of time for a breast pump according to prior art without a positive pressure.
Figure 13:
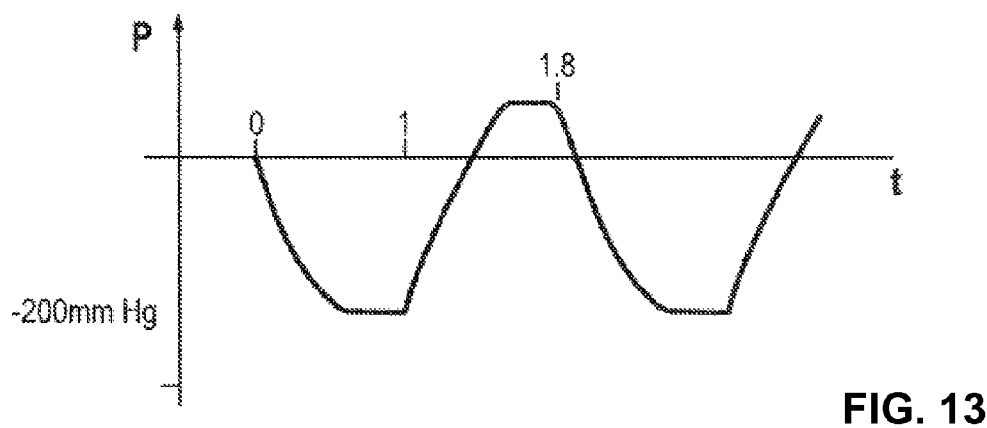
FIG. 13 shows a graphic view of the pressure as a function of time for a breast pump according to prior art with a positive pressure.
Figure 14:
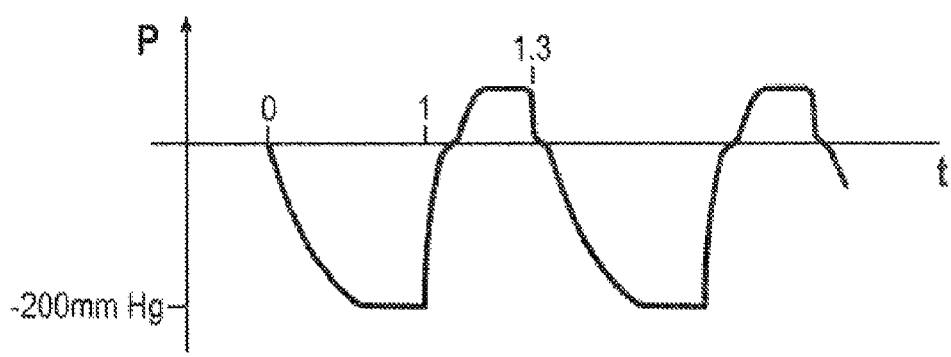
FIG. 14 shows a graphic view of the pressure as a function of time for a breast pump according to the invention.

FIG. 11 presents a third exemplary embodiment. It corresponds to the solution according to FIGS. 8 to 10, except that surface elements 98 with film hinges 980 are used in place of leaf springs. For example, these surface elements 98 can be made out of metal or plastic.

The suction pump unit according to the invention with the switching valve permits passive and active ventilation of the output line connected with the output.

The invention claimed is:

1. A suction pump unit comprising:
a vacuum port;
an excess pressure port; and
a switching valve, wherein the switching valve comprises a valve body with a first input and a second input, wherein the first input is connected with the vacuum port, and the second input is connected with the excess pressure port, and wherein the switching valve comprises an output defining a through hole, wherein the output can be moved relative to the inputs from the first input to the second input and back, such that the through hole alternately establishes a fluid-communicating connection with one of the first input or the second input, wherein the through hole of the output is released and ventilated during at least part of the movement of the output between the first input and the second input, and wherein the switching valve comprises a first electromagnet with a first coil and a second electromagnet with a second coil, wherein each coil is interspersed by a ferromagnetic, hollow core, wherein a first core forms the first input and a second core forms the second input, and wherein the output comprises a permanent magnet.

2. The suction pump unit according to claim 1, wherein the output can be lifted relative to the first input and the second input while moving between the two inputs, wherein the through hole of the output is released and ventilated in the lifted state.

3. The suction pump unit according to claim 1, wherein the valve body is fixed in place in the suction pump unit, and the output is movable.

4. The suction pump unit according to claim 1, wherein the movement of the output relative to the first input and the second input involves a combination of being shifted along a straight line in a first direction and being lifted in a second direction perpendicular to the first direction.

5. The suction pump unit according to claim 1, wherein an output line of the suction pump unit is secured to the output, wherein the output line can be moved together with the output.

6. The suction pump unit according to claim 1, further comprising a single vacuum pump, wherein the vacuum pump comprises the vacuum port, and wherein it further comprises an exhaust which forms the excess pressure port.

7. The suction pump unit according to claim 1, wherein the first input and the second input are arranged next to each other in a common plane.

8. The suction pump unit according to claim 1, wherein the first input and the second input are arranged in a sliding plate with a planar surface, and the output rests upon the sliding plate when the fluid-communicating connection is established with one of the first input or the second input.

9. The suction pump unit according to claim 1, wherein the permanent magnet is a ring that defines the through hole.

10. The suction pump unit according to claim 1, wherein the first input and the second input of the valve body are covered by a lid, wherein the lid defines a hollow space over the first input and the second input, and wherein the output is movably held in the hollow space.

11. The suction pump unit according to claim 10, wherein the hollow space is subjected to ambient air.

12. The suction pump unit according to claim 10, wherein the hollow space comprises a height that exceeds a thickness of the output.

13. The suction pump unit according to claim 1, wherein the first coil and the second coil are held in a shared yoke, wherein the yoke is arranged at an end of the valve body lying opposite the output.

14. A method for operating a suction pump unit, wherein the suction pump unit comprises a vacuum port, an excess pressure port and a switching valve, wherein the switching valve comprises a valve body with two inputs, wherein a first of the inputs is connected with the vacuum port, and a second of the inputs is connected with the excess pressure port, and wherein the switching valve comprises an output with a through hole, wherein the switching valve comprises a first electromagnet with a first coil and a second electromagnet with a second coil, wherein each coil is interspersed by a ferromagnetic, hollow core, wherein a first core forms the first input and a second core forms the second input, and wherein the output comprises a permanent magnet:
 moving the output relative to the two inputs, such that the output moves back and forth between the two inputs;
 the through hole alternately establishing a fluid-communicating connection with one of the two inputs during the movement of the output; and
 releasing and ventilating the through hole of the output during the movement between the two inputs.

15. A suction pump unit comprising:
 a suction pump comprising a vacuum port and an exhaust;
 a switching valve comprising a valve body and a lid, wherein the valve body comprises a sliding plate, a first electromagnet defining a first hollow core, and a second electromagnet defining a second hollow core, wherein the sliding plate defines a first through hole in axial alignment with the first core and a second through hole in axial alignment with the second core, wherein the lid is disposed on the sliding plate, wherein the lid defines a hollow space between the sliding plate and an inwardly directed surface of the lid, wherein the hollow space is sized and shaped to permit a magnetic ring defining a through hole to be moved between the first through hole to the second through hole of the sliding plate, and wherein the magnetic ring is passively ventilated while moving between the first through hole and the second through hole of the sliding plate;
 a suction line with a first end and a second end, wherein the first end of the suction line is coupled to the vacuum port and the second end of the suction line is coupled to the switching valve;
 a pressure line with a first end and a second end, wherein the first end of the pressure line is coupled to the exhaust and the second end of the pressure line is coupled to the switching valve; and
 an electronic controller in communication with the suction pump and the switching valve.

16. A suction pump unit comprising:
 a suction pump comprising a vacuum port and an exhaust;
 a switching valve comprising a first plate and a second plate connected by two flexible parts, wherein an outlet is coupled to and centrally located in the first plate, wherein the second plate defines a first through hole and a second through hole, wherein the switching valve is in the shape of a parallelogram when the outlet forms a fluid communicating connection with one of the first through hole or the second through hole, wherein the two flexible parts shift the first plate under the application of force such that the outlet is capable of moving back and forth between the first through hole and the second through hole, wherein the outlet is lifted above the second plate and passively ventilated while moving between the first through hole and the second through hole;
 a suction line with a first end and a second end, wherein the first end of the suction line is coupled to the vacuum port and the second end of the suction line is coupled to the switching valve;
 a pressure line with a first end and a second end, wherein the first end of the pressure line is coupled to the exhaust and the second end of the pressure line is coupled to the switching valve; and
 a drive coupled to a driving rod, wherein the driving rod is coupled to or abuts the first plate.

17. A suction pump unit comprising:
 a vacuum port;
 an excess pressure port; and
 a switching valve, wherein the switching valve comprises a valve body with a first input and a second input, wherein the first input is connected with the vacuum port, and the second input is connected with the excess pressure port, and wherein the switching valve comprises an output defining a through hole, wherein the output can be moved relative to the inputs from the first input to the second input and back, such that the through hole alternately establishes a fluid-communicating connection with one of the first input or the second input, wherein the through hole of the output is released and ventilated during at least part of the movement of the output between the first input and the second input, and wherein the output can be lifted relative to the first input and the second input while moving between the two inputs, wherein the through hole of the output is released and ventilated in the lifted state.

18. A suction pump unit comprising:
 a vacuum port;
 an excess pressure port; and
 a switching valve, wherein the switching valve comprises a valve body with a first input and a second input, wherein the first input is connected with the vacuum port, and the second input is connected with the excess pressure port, and wherein the switching valve comprises an output defining a through hole, wherein the output can be moved relative to the inputs from the first input to the second input and back, such that the through hole alternately establishes a fluid-communicating connection with one of the first input or the second input, wherein the through hole of the output is released and ventilated during at least part of the movement of the output between the first input and the second input, and wherein the valve body is fixed in place in the suction pump unit, and the output is movable.

19. The suction pump unit according to claim 18, wherein the switching valve comprises a first plate and a second plate that are arranged parallel to each other and can be shifted parallel to each other, wherein the output is held in the first plate, and the first input and the second input are situated in the second plate.

20. The suction pump unit according to claim 19, wherein the two plates are connected with each other to form a parallelogram by means of flexural elements.

21. The suction pump unit according to claim 20 wherein the flexural elements are leaf springs or surface elements with film hinges.

22. The suction pump unit according to claim 19, wherein at least one of the first plate or the second plate can be moved in the direction of a plane of the moving plate through the exertion of force, and wherein the moving plate allows the output to move relative to and back and forth between the first input and the second input.

* * * * *